(12) United States Patent
Berg

(10) Patent No.: US 12,230,235 B2
(45) Date of Patent: Feb. 18, 2025

(54) MULTI FREQUENCY HARMONIZATION DEVICE

(71) Applicant: Sigmar Berg, Malibu, CA (US)

(72) Inventor: Sigmar Berg, Malibu, CA (US)

(73) Assignee: LOVETUNER, INC., Malibu, CA (US)

( * ) Notice: Subject to any disclaimer, the term of this patent is extended or adjusted under 35 U.S.C. 154(b) by 342 days.

(21) Appl. No.: 17/351,167

(22) Filed: Jun. 17, 2021

(65) Prior Publication Data

US 2021/0407471 A1    Dec. 30, 2021

Related U.S. Application Data

(60) Provisional application No. 63/046,566, filed on Jun. 30, 2020.

(51) Int. Cl.
| | | |
|---|---|---|
| *G10D 7/06* | (2020.01) | |
| *A61M 21/02* | (2006.01) | |
| *G10G 5/00* | (2006.01) | |
| *A61M 21/00* | (2006.01) | |

(52) U.S. Cl.
CPC .............. *G10D 7/06* (2013.01); *A61M 21/02* (2013.01); *G10G 5/005* (2013.01); *A61M 2021/0027* (2013.01)

(58) Field of Classification Search
CPC .. G10D 7/06; A61M 21/02; A61M 2021/0027
See application file for complete search history.

(56) References Cited

U.S. PATENT DOCUMENTS

| | | | | |
|---|---|---|---|---|
| 1,125,502 A | * | 1/1915 | Fillmore | G10G 7/02 84/456 |
| 1,366,735 A | * | 1/1921 | Kratt | G10G 7/02 984/260 |
| 1,538,336 A | * | 5/1925 | Kratt | G10G 7/02 984/260 |
| 1,697,500 A | * | 1/1929 | Friend | G10H 3/12 84/723 |
| 2,726,568 A | * | 12/1955 | Lake | G10D 7/14 84/456 |
| 2,837,954 A | * | 6/1958 | Kratt | G10G 7/02 984/260 |
| 2,871,747 A | * | 2/1959 | Kratt | G10G 7/02 984/260 |
| 2,871,748 A | * | 2/1959 | Kratt | G10G 7/02 984/260 |
| 4,211,031 A | | 7/1980 | Gambino | |
| 4,915,660 A | | 4/1990 | Overholt, Sr. | |
| 5,222,903 A | | 6/1993 | Parrot et al. | |
| 6,231,418 B1 | | 5/2001 | Hancock et al. | |

(Continued)

FOREIGN PATENT DOCUMENTS

JP    2017068110 A    4/2017

*Primary Examiner* — Robert W Horn
(74) *Attorney, Agent, or Firm* — ORBIT IP, LLP

(57) ABSTRACT

A device includes two or more units, with each unit connected to one or more other units, each of which includes a cap, a tube coupled to the cap and a reed coupled to the tube. Each tube generates at least one sound frequency and can also include harmonics of that single frequency. Airflow through the body oscillates the reed to produce an audible tone from the device.

19 Claims, 2 Drawing Sheets

(56) References Cited

U.S. PATENT DOCUMENTS

| | | | | |
|---|---|---|---|---|
| 6,245,981 | B1* | 6/2001 | Smith | G09B 15/005 |
| | | | | 84/474 |
| 9,012,752 | B2* | 4/2015 | Priest | G09B 15/00 |
| | | | | 84/470 R |
| 11,986,601 | B2* | 5/2024 | Berg | G10D 7/06 |
| 2004/0163693 | A1* | 8/2004 | Uemura | A63C 11/2228 |
| | | | | 135/72 |
| 2007/0006613 | A1* | 1/2007 | Hirsch | A44B 15/00 |
| | | | | 63/4 |
| 2013/0319206 | A1* | 12/2013 | Priest | G09B 15/00 |
| | | | | 84/470 R |
| 2021/0407471 | A1* | 12/2021 | Berg | G10D 9/10 |

\* cited by examiner

MULTI FREQUENCY HARMONIZATION DEVICE

CROSS-REFERENCE TO RELATED PATENT APPLICATIONS

Embodiments of the present invention relate to U.S. Provisional Application Ser. No. 63/046,566, filed Jun. 30, 2020, entitled "MULTI-FREQUENCY HARMONIZATION DEVICE", the contents of which are incorporated by reference herein in its entirety and which is a basis for a claim of priority.

FIELD OF THE INVENTION

Embodiments of the present disclosure generally relate to a system and method for meditative and self-healing devices and techniques, and more specifically to devices and methods for sound production at specific frequencies, which positively affect human physical and mental well-being.

BACKGROUND OF THE INVENTION

Studies have confirmed that sound at specific frequencies can have a therapeutic effect on human body and mind, including on physical organs as well as the nervous system and the brain. Use of sound as a therapeutic method and technique to promote and support relaxation and healing is known to have been practiced by humans for thousands of years.

The science of sound therapy and its impact on humans is premised on the fact that matter in all forms, at the atomic, molecular, and macromolecular level, is in a constant state of motion, and that humans are impacted by sound that is directed to them. Studies have confirmed that sound at specific frequencies can positively impact humans both physiologically and psychologically through its impact on the nervous system and the brain. Sound therapy has received renewed attention and focus on recent decades as increasing lifestyle automation and the onset of the age of information age, has resulted in elevated levels of stress experienced by a growing share of the world's population. Many have found sound therapy to be highly effective for its healing and relaxing effects.

Human body is composed of 70% water and several pounds of air. Sound travels in waves through media such as air and water and transfers its energy through vibration of particles through which it travels. There is a direct relationship between sound energy and frequency, which is measured in units of hertz (Hz). The range of hearing for humans is between 20 Hz and 20,000 Hz. Studies and experience confirm that certain sound frequencies "resonate" with human organs, mind, and the nervous system with resulting therapeutic healing and relaxation impact. These targeted frequencies can be delivered via human voice, such as singing, through sound creating tools and through devices such as tuning forks, musical instruments, etc.

SUMMARY OF THE DISCLOSURE

Various embodiments of the present disclosure are directed to an inventive method and apparatus that includes a device comprised of two or more connected units, with each unit designed to create sound in a certain single frequency in response to air or gas flow through the unit.

Each unit includes a body, a cap coupled to the body, and a reed coupled to the body. Air flow through the body causes the reed to oscillate and produce an audible tone. Each unit of the device is designed to create a tone in a single frequency and could also include an additional harmonic of that frequency. The frequency generated by each unit in the device is different from the frequency of other units of the device.

A person skilled in the art would readily appreciate that the present disclosure may be a basis for modifying or designing other structures for carrying out the same purposes of the present disclosure. Such equivalent constructions do not depart from the teachings of the disclosure as set forth in the present specification, drawings, and claims. The novel features, which are believed to be characteristic of the disclosure, both as to its organization and method of operation, together with further purposes and advantages, will be better understood from the following description when considered in connection with the figures provided herein.

A person skilled in the art would appreciate that these figures are provided for the purposes of illustration and description only and are not intended to act as limits of the present disclosure.

DETAILED DESCRIPTION OF THE PREFERRED EMBODIMENTS

The following description is not to be interpreted or applied in a limiting sense, but as an illustration of the general principles and aspects of the invention. The breadth and scope of the present inventions are set forth by the claims. Various inventive features are described below that can each be used independently of one another or in combination with other disclosed and undisclosed features.

Figure 1:
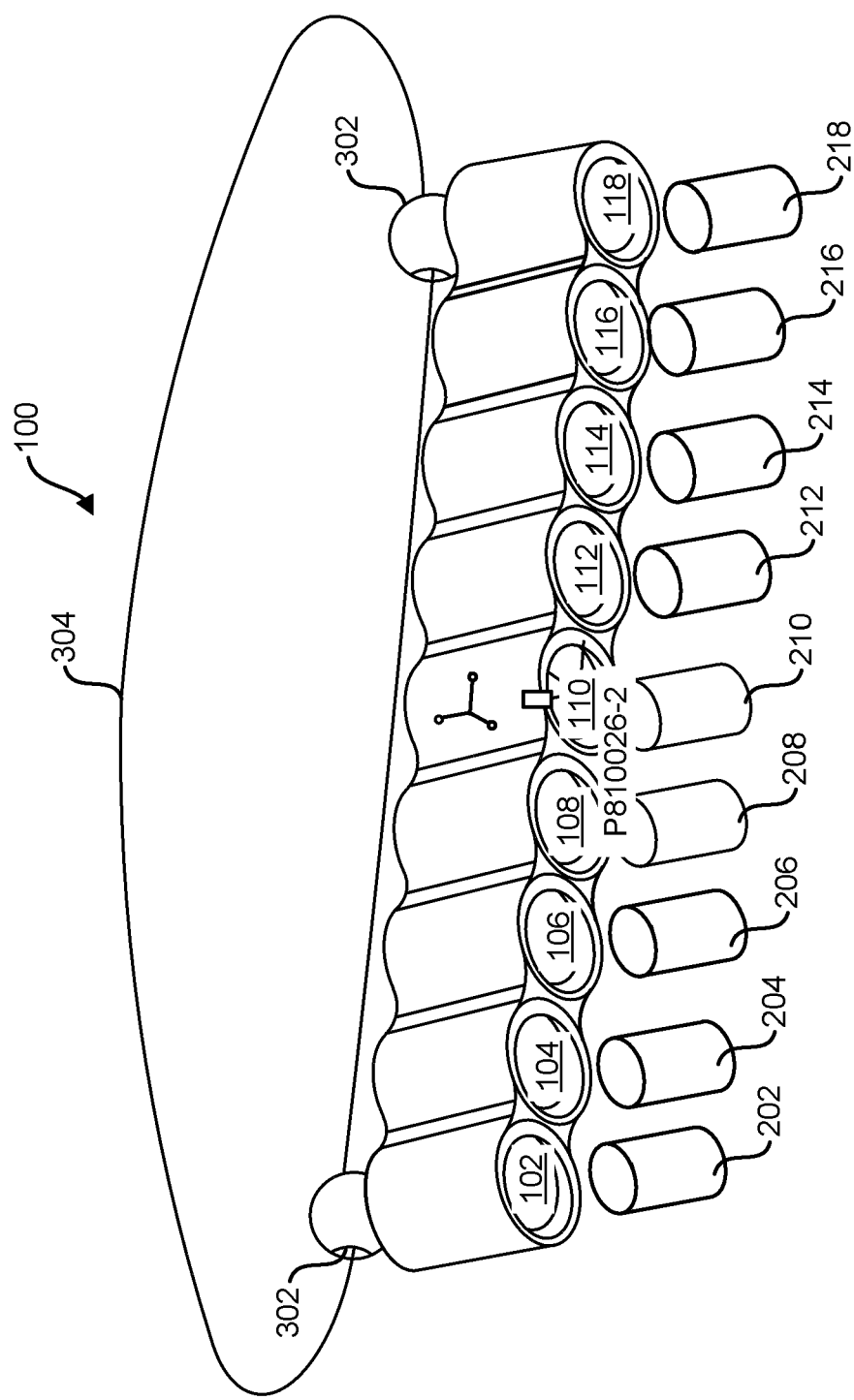
FIG. 1 is a schematic diagram according to an exemplary embodiment of the present disclosure.

FIG. 1 depicts an embodiment of the present disclosure. Device 100 comprises nine units. Each unit comprises a tube, identified by reference numerals 202, 204, 206, 208, 210, 212, 214, 216 and 218, which couples to a corresponding cap, identified by reference numerals 102, 104, 106, 108, 110, 112, 114, 116 and 118. Each unit is connected to at least one other unit. Each tube 202 is depicted in cylindrical shape, but may be in various other shapes, including square, hexagonal, conical, etc. Optionally, caps 102 and 118, located on units located at each end of the device 100, are each coupled to ring 302 that can fit a chain 304 for easy carrying of device 100.

Tube 202, etc., may be made from any suitable solid material, such as steel, brass, copper, aluminum, wood, tin, ceramics, or a combination of materials. Tube 202, etc. may also be coated with another material, e.g., chrome, aluminum, ceramic, or combination of materials. Tube 202 may be of any length, but often is of a length that is easily carried and/or worn by a person. Although shown as cylindrical, tube 202 may also take other shapes, e.g., square, hexagonal, conical, etc.

Cap 102, etc. may be made from any suitable material, such as steel, brass, copper, aluminum, wood, tin, ceramics, or a combination of materials. Cap 102, etc. may also be coated with another material such as chrome, aluminum, ceramic, or combination of materials. Cap 102, etc. may have a design, logo, or other ornamental embellishment as desired.

Although shown as being flat, cap 104, etc. may also take other shapes, e.g., tapered, square, hexagonal, conical, etc. Cap 104, etc. contacts tube 102, etc. and may cover at least one end of tube 202, etc.

Ring 302 and chain 304 may be used as ornamental and/or functional portions of device 100. In an aspect of the present disclosure, taper 302 and ring 304 may provide ease of carrying device 100. For example, and not by way of limitation, ring 302 is used to place device 100 on a necklace-length chain 304 such that device 100 is available to a user at various times during any given day. Chain 304 may be a chain, such as a steel-ball chain, nickel plated chain, stainless steel chain, silver chain, gold chain, copper chain, brass chain, leather cord, waxed cotton cord, hemp string, wooden ball chain, gemstone chain comprising additional devices such as crystals, quartz, gems, etc., a mala bead chain, a glass ball chain, and/or other types of devices for holding device 100. Chain may also be made of one or more materials, and/or may also be a cord, rope, and/or other length of material without departing from the scope of the present disclosure. Further, chain 304 may be of any length as desired.

Figure 2:
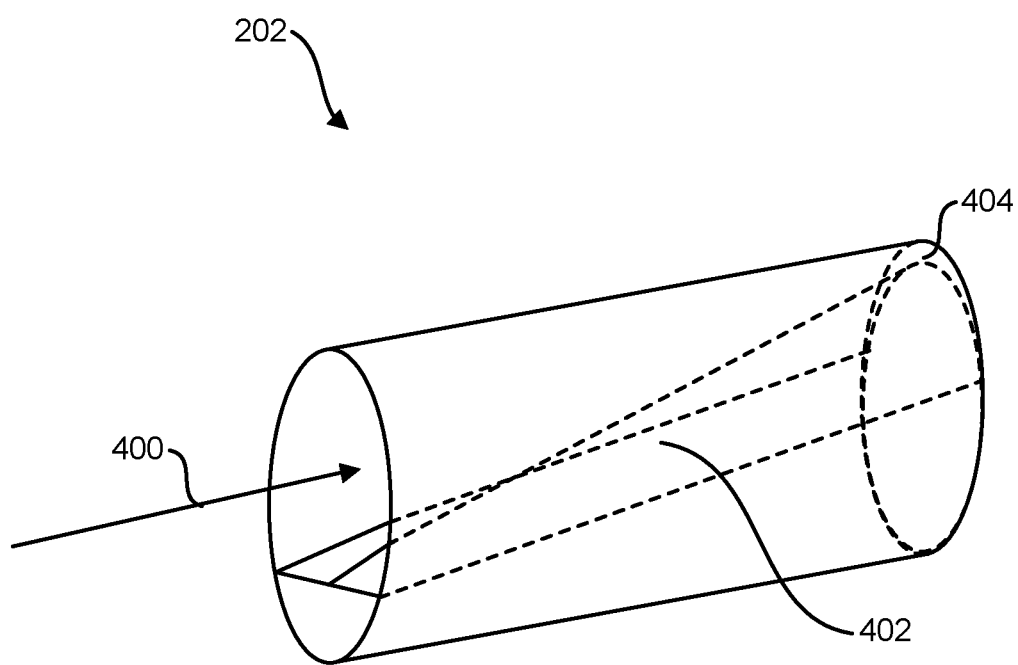
FIG. 2 is a schematic diagram according to an exemplary embodiment of the present disclosure.

By reference to FIG. 2, which depicts one tube 202 of the device 100 as an example, reed 402 is inserted in tube 202 and vibrates in response to airflow in direction 400 to produce a single frequency sound, and/or a single frequency with harmonics of the single frequency, at outlet 404.

Tube 202 and reed 402 may be combined in a way, which produces a specific, desired tone. Such frequencies include, but are not limited to, 174 Hertz (Hz), 285 Hz, 396 Hz, 417 Hz, 528 Hz, 639 Hz, 741 Hz, 852 Hz and/or 963 Hz.

Typically, airflow originates from breathing by user into tube 202. By coupling the user's breath with the tube 202, the user may be more closely harmonized and/or coupled with the frequency that tube 202 produces, which may have a more profound effect on the user than having the frequency generated externally, e.g., via a speaker or other external source.

Although FIG. 2 illustrates airflow in direction 400, which may be produced on an exhale of a user, the airflow may be in other directions, e.g., opposite of direction 400, in addition to and/or instead of the airflow in direction 400. Such other airflows may be produced on an inhale of a user. Further, the note and/or tone produced in direction 400 may be different than the note and/or tone produced when airflow is in a direction other than direction 400.

Each tube 202-218 size, length, materials, etc., in combination with reed 402 size, width, length, etc., may produce a specific, desired tone. Such frequencies include, but are not limited to, 174 Hertz (Hz), 285 Hz, 396 Hz, 417 Hz, 528 Hz, 639 Hz, 741 Hz, 852 Hz, and/or 963 Hz. In an aspect of the present disclosure, tube 202 may be at the lowest frequency, and the frequencies of each subsequent tube in the device 100 may be the next higher frequency that device 100 can produce. For example, and not by way of limitation, tube 202 may produce 174 Hz, tube 204 may produce 285 Hz, tube 206 may produce 396 Hz, etc. In another aspect of the present disclosure, the frequencies may be in inverse order, such that tube 202 produces the highest frequency, and the frequency of each subsequent tube may be the next lower frequency that device 100 can produce. In another aspect of the present disclosure, the frequencies produced by tubes 202-218 may be in a random order, or in a desired order.

A user may wish to produce both 396 Hz and 639 Hz at the same time, and thus would blow into both tubes 202 and 204. Many combinations of which tube 202-218 produces which frequency of interest are possible without departing from the scope of the present disclosure.

In an aspect of the present disclosure, tubes 20-218 produce frequencies that are considered healing and/or harmonization frequencies that correspond to the chakras and/or chakra colors of the body. By producing one or more of the healing and/or harmonization frequencies with device 100, the user's body "tunes" itself to that frequency and may stimulate the chakra associated with that frequency. In an aspect of the present disclosure, producing multiple healing and/or harmonization frequencies, either in series and/or parallel, multiple chakras may be stimulated.

A person of skill in the art of the present invention would appreciate that device 100 differs from other devices, e.g., flutes, recorders, other wind instruments, etc., as these devices are used to create various notes and play in various tempos. A device in accordance with the present invention is designed, at least in part, to play a single note (with or without harmonics of the note) in a long, steady fashion from each tube 202, 204, 206, 208, 210, 212, 214, 216 and 218. Further, the breathing exercises and lack of other muscle usage (finger movement, tongue staccato playing, etc.) that may be used to create long, steady, single-tone notes may assist in creating desired effects from device 100.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A device for generating a plurality of individual calming and healing tones at a single frequency comprising:
   a plurality of separate cylindrically shaped bodies wherein each body in the plurality of bodies has a reed coupled thereto;
   wherein airflow through any body in the plurality of bodies oscillates the reed coupled thereto and produces an audible tone at a single frequency from the body;
   wherein each body in the plurality of bodies produces a different single frequency; and
   a cap comprising a plurality of cavities wherein each cavity in the plurality of cavities is designed to removably hold a body in the plurality of bodies such that each body in the plurality of bodies may be repeatedly inserted and withdrawn from the cap.

2. The device of claim 1, wherein the audible tone further comprises at least one harmonic of the single frequency.

3. The device of claim 1, wherein the single frequency is selected from a group consisting of 174 Hertz (Hz), 285 Hz, 396 Hz, 417 Hz, 528 Hz, 639 Hz, 741 Hz, 852 Hz and 963 Hz.

4. The device of claim 3, further comprising a first ring and second ring coupled to the cap at each end of the cap, wherein the first ring and second ring are designed to accepts an apparatus for carrying the device.

5. The device of claim 4, wherein the apparatus comprises a chain.

6. The device of claim 3, wherein the airflow is provided by a user's breath.

7. A device for generating a plurality of individual calming and healing tones at a single frequency comprising:

a plurality of individual separate and distinct bodies wherein each body in the plurality of bodies has a reed coupled thereto;

wherein airflow through any body in the plurality of individual separate and distinct bodies oscillates the reed coupled thereto and produces an audible tone at a single frequency from the body;

wherein each body in the plurality of individual, separate and distinct bodies produces a different single frequency; and a cap comprising a plurality of cavities wherein each cavity in the plurality of cavities is designed to removably hold a body in the plurality of individual, separate and distinct bodies such that each body in the plurality of individual, separate and bodies may be repeatedly inserted and withdrawn from the cap.

8. The device of claim 7, wherein the audible tone further comprises at least one harmonic of the single frequency.

9. The device of claim 7, wherein the single frequency is selected from a group consisting of 174 Hertz (Hz), 285 Hz, 396 Hz, 417 Hz, 528 Hz, 639 Hz, 741 Hz, 852 Hz and 963 Hz.

10. The device of claim 7, further comprising a first ring and second ring coupled to the cap at each end of the cap, wherein the first ring and second ring are designed to accept an apparatus for carrying the device.

11. The device of claim 7, wherein the apparatus comprises a chain.

12. The device of claim 7, wherein the airflow is provided by a user's breath.

13. The device of claim 7, wherein a cross-section of any body in the plurality of individual separate and distinct bodies is selected from the group consisting of circular, oval, square and hexagonal.

14. A device for generating a plurality of individual calming and healing tones at a single frequency comprising:

a plurality of separate bodies wherein each body in the plurality of bodies has a reed coupled thereto;

wherein airflow through any body in the plurality of separate bodies oscillates the reed coupled thereto and produces an audible tone at a single frequency from the body wherein the single frequency is selected from a group consisting of 174 Hertz (Hz), 285 Hz, 396 Hz, 417 Hz, 528 Hz, 639 Hz, 741 Hz, 852 Hz and 963 Hz.;

wherein each body in the plurality of separate bodies produces a different single frequency; and a cap comprising a plurality of cavities wherein each cavity in the plurality of cavities is designed to removably hold a body from the plurality of separate bodies such that each body in the plurality bodies may be repeatedly inserted and withdrawn from the cap.

15. The device of claim 14, wherein the audible tone further comprises at least one harmonic of the single frequency.

16. The device of claim 14, further comprising a first ring and second ring coupled to the cap at each end of the cap, wherein the first ring and second ring are designed to accept an apparatus for carrying the device.

17. The device of claim 14, wherein the apparatus comprises a chain.

18. The device of claim 14, wherein the airflow is provided by a user's breath.

19. The device of claim 14, wherein a cross-section of any body in the plurality of separate bodies is selected from the group consisting of circular, oval, square and hexagonal.

* * * * *